(12) United States Patent
Joyce

(10) Patent No.: US 6,347,401 B1
(45) Date of Patent: Feb. 19, 2002

(54) FACE PIECE PROTECTION SYSTEM

(76) Inventor: John Joyce, 19 Baldwin Blvd., Bayville, NY (US) 11709

( * ) Notice: Subject to any disclaimer, the term of this patent is extended or adjusted under 35 U.S.C. 154(b) by 0 days.

(21) Appl. No.: 09/681,646

(22) Filed: May 15, 2001

(51) Int. Cl.[7] .......................... A61F 9/00; A41D 27/12
(52) U.S. Cl. ............................................. 2/15; 2/46
(58) Field of Search ............................ 2/15, 46, 455, 2/209.13

(56) References Cited

U.S. PATENT DOCUMENTS

| | | | |
|---|---|---|---|
| 4,579,113 A | * | 4/1986 | McCreadie et al. |
| 4,983,436 A | * | 1/1991 | Bailey et al. |
| 5,100,709 A | * | 3/1992 | Barger et al. |
| 5,155,863 A | * | 10/1992 | Roberts |
| 5,408,995 A | | 4/1995 | Contino et al. |
| 5,592,937 A | | 1/1997 | Freund |
| 5,628,308 A | | 5/1997 | Harges, Jr. et al. |
| 5,673,433 A | * | 10/1997 | Rothrum |
| 5,732,414 A | * | 3/1998 | Monica |
| 5,794,617 A | | 8/1998 | Brunell et al. |
| 6,016,804 A | | 1/2000 | Gleason et al. |

FOREIGN PATENT DOCUMENTS

JP              84477           *  3/2000

* cited by examiner

Primary Examiner—Rodney M. Lindsey
(74) Attorney, Agent, or Firm—Collard & Roe, P.C.

(57) ABSTRACT

A thin protective sheet for covering a face plate on an air mask. This thin sheet can come in many forms. For example, in a first embodiment, the sheet comprises a substantially rectangular thin sheet of plastic having a first edge with two substantially circular cut outs, and a second oppositely spaced edge having two substantially square cut outs and a substantially semi-circular cut out. In addition, there are positioned normal to these two sheets, two parallel spaced substantially flat edges. In the second embodiment of the invention, the sheet is a substantially rectangular thin sheet of plastic having an edge having a series of curves. There is also a second oppositely spaced flat edge and two oppositely spaced substantially flat edges positioned normal to the first edge and the second edge. The third embodiment is oval shaped and is designed to fit around a mask as well.

14 Claims, 4 Drawing Sheets

FACE PIECE PROTECTION SYSTEM

BACKGROUND OF INVENTION

The invention relates to a cover for covering over a user's mask for an air pack. This cover could be formed from a clear plastic strip such as mylar. Masks are known in the art. For example, air masks are shown in U.S. Pat. Nos. 5,408,995; 5,592,937; 5,628,308; 5,794,617; and 6,016,804 incorporated herein by reference.

When masks for air packs are not being used, the face plates, which are usually made from clear plastic, can become scratched or nicked, thereby hindering the viewing ability of the user wearing these face plates. Therefore, a user would want to protect any damage to these face plates by applying a protective layer to these face plates.

SUMMARY OF INVENTION

Essentially the invention relates to a protective covering for a face screen. This protective covering is designed as a thin sheet of flexible self adhering material shaped to fit over the mask to protect the face screen for the mask. This material is made from flexible plastic such as mylar. This protective covering comprises a series of fasteners for attaching the self adhering material to the mask. These fasteners are selected from the group consisting of: either double sided tape or a hook and loop fastener.

This material could either be transparent or simply opaque but translucent. In addition, this material could take on a red tint or the material could be frosted to help users such as firefighters simulate a live fire while still conducting training drills.

Essentially the thin sheet can come in two forms. For example, in a first embodiment, the sheet comprises a substantially rectangular thin sheet of plastic such as mylar having a first edge with two substantially circular cut outs, and a second oppositely spaced edge having two substantially square cut outs and a substantially semi-circular cut out. In addition, there are positioned normal to these two sheets, two opposite parallel spaced flat edges.

In the second embodiment, the sheet is a substantially rectangular thin sheet of plastic having a substantially flat first edge. There is also an oppositely spaced second edge having a series of curves and two oppositely spaced substantially flat edges positioned normal to the first edge and the second edge.

In the third embodiment of the invention, the sheet is shaped substantially oval to cover an oval shaped mask.

BRIEF DESCRIPTION OF DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings wherein similar reference characters denote similar elements throughout the several views.

DETAILED DESCRIPTION

Figure 1:
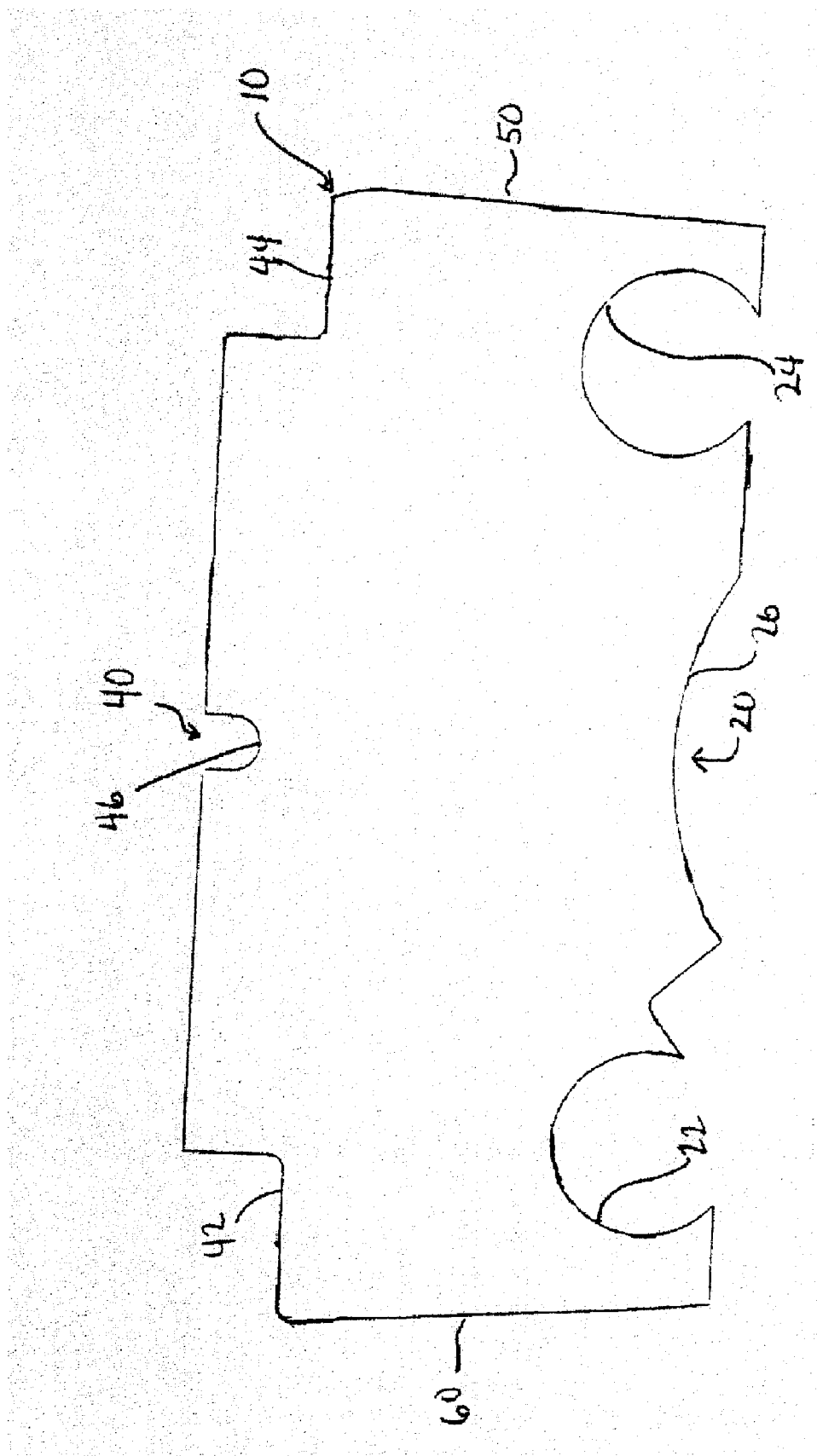
FIG. 1 shows a front view of the first embodiment of the invention.

FIG. 1 is a front view of the first embodiment of the invention which is essentially a flat sheet 10. Flat sheet 10 is made from a plastic based material such as mylar. Flat sheet 10 has a first edge 20, a second edge 40, and two oppositely spaced side edges 50 and 60 positioned normal to first edge 20 and second edge 40.

First edge 20 includes two substantially circular shaped holes 22 and 24 cut out so that these cut outs or holes 22 and 24 wrap around voice emitters on a mask. In addition, there are also a rounded edge 26 cut to fit over a regulator cut-out on a user's mask. Thus, this first edge is customized to fit over a particular face plate on a user's mask.

Second edge 40 contains two substantially rectangular cut outs 42 and 44 disposed on each corner of flat sheet 10 adjacent to side edges 50 and 60. Flat sheet 10 includes cut outs 42 and 44 to accommodate screws disposed on the face plate for screwing a net onto the face plate. Second edge 40 also contains a semi-circular cut out 46 which allows sheet 10 to fit around a screw designed to hold a face plate to the mask. Side edges 50 and 60 are designed substantially flat because the side edges of the mask are also substantially flat.

Figure 2:
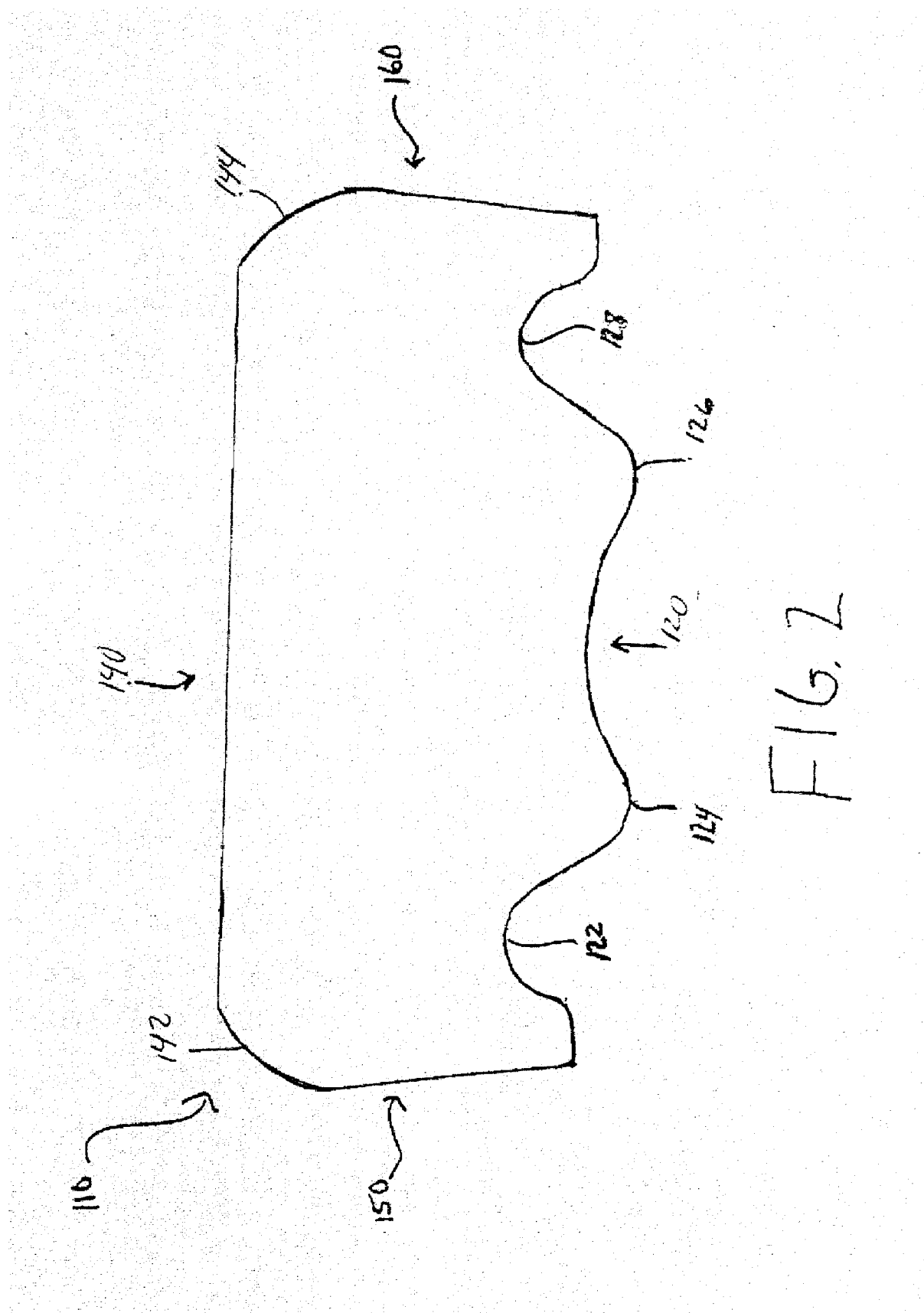
FIG. 2 shows a front view of the second embodiment of the invention.

FIG. 2 is a front view of the second embodiment of the invention 110. With this design, there is a rounded first edge 120 and a second edge 140 spaced opposite first edge 120. Side edges 150 and 160 are spaced opposite each other and join with second edge 140 to form rounded corners 142 and 144. Second edge 140 and side edges 150 and 160 are shaped substantially flat. However, first edge 120 has a series of curves 122, 124, 126 and 128 with curves 122 and 128 extending inward to accommodate a plurality of voice emitters on a mask while curves 124 and 126 extend out of sheet 110 to cover the remaining portion of the mask.

Figure 3:
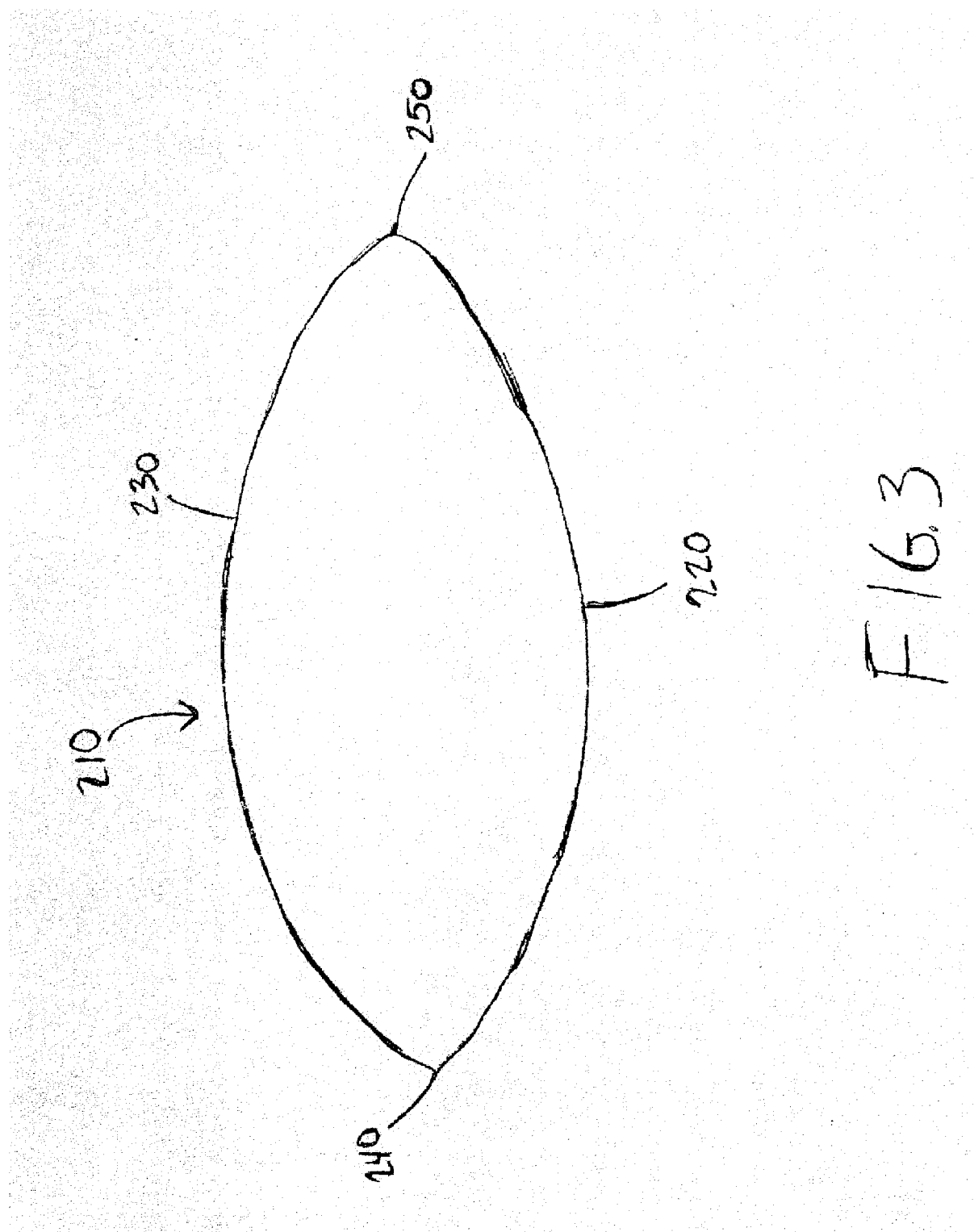
FIG. 3 shows a third embodiment of the invention.
Figure 4:
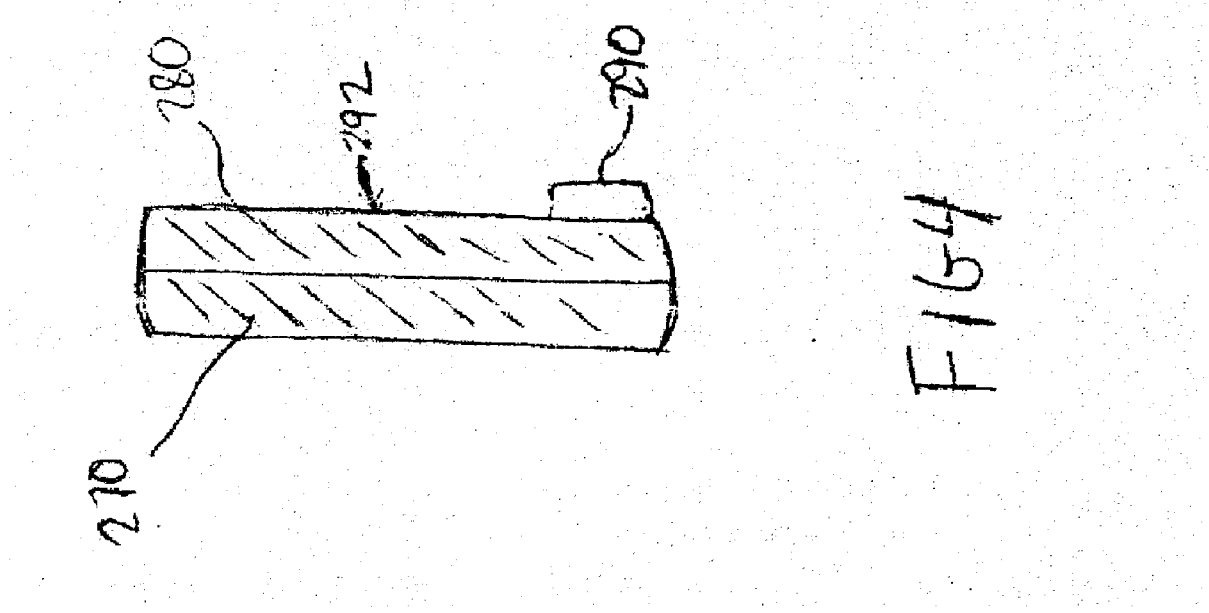
FIG. 4 shows a side view of the invention.

FIG. 3 shows a third embodiment of the invention wherein there is shown an oval or football shaped mask 210 having a first curved edge 220 and an opposite curved edge 230. These edges 220 and 230 join at connection points 240 and 250 to form a substantially oval shaped piece. As shown in FIG. 4, all three embodiments can have a first face 270 that is frosted or colored, and a second face 280 that can either receive a fastener 290 such as a hook and loop fastener, or double sided tape. Second face can also contain an adhesive 292 to attach to a face mask.

First embodiment 10 second embodiment 110 and third embodiment 210, are particularly designed to fit around a face plate on a mask. Because of the unique shape of both first embodiment 10, second embodiment 110, and third embodiment 210, this thin sheet can fit onto the face plate of a mask and cover a person's mask protecting it from scratches, nicks, scrapes, or any other damage from use. In this case, the material could be tinted bright orange on a portion or on the entire surface to indicate to the user that the material is on the mask. In addition, these sheets could also be frosted or tinted to aid in drills or training exercises. For example, embodiments 10, 110 and 210 could be frosted to simulate a smoke filled room. In addition, embodiments 10, 110, and 210 could also be tinted either red or bright orange to simulate a fire in the room.

Accordingly, while a plurality of embodiments of the present invention have been shown and described, it is to be understood that many changes and modifications may be made thereunto without departing from the spirit and scope of the invention as defined in the appended claims.

I claim:

1. A protective covering for a face screen on a mask comprising:

a thin sheet of self adhering material shaped to fit over the mask to protect the face screen of the mask.

2. The protective covering as in claim 1, wherein said material is made out of plastic.

3. The protective covering as in claim 2, wherein said material is made out of mylar.

4. The protective covering as in claim 1, further comprising a series of fasteners coupled to the material for attaching said self adhering material to the mask.

5. The protective covering as in claim 1, wherein said material is transparent.

6. The protective covering as in claim 1, wherein said material is translucent.

7. The protective covering as in claim 1, wherein said material has a red tint.

8. The protective covering as in claim 1, wherein said material has an orange tint.

9. The protective covering as in claim 4, wherein said fasteners are selected from the group consisting of: hook and loop fasteners, or double sided tape.

10. The protective covering as in claim 1, wherein said thin sheet has a substantially flat edge and an opposite edge having a series of curves to conform to the mask.

11. The protective covering as in claim 1, wherein said thin sheet has at least two substantially circular holes cut out so as to attach over a plurality of voice emitters on the mask.

12. A protective covering for a face screen on a mask comprising:

a substantially rectangular thin sheet of plastic having a first edge with two substantially circular cut outs, a second oppositely spaced edge having two substantially square cut outs and a substantially semi-circular cut out and two opposite parallel spaced substantially flat edges positioned normal to said first edge and said second edge.

13. The protective covering as in claim 12, wherein said substantially square cut outs are to accommodate screws on the mask, and said semi-circular cut outs are to accommodate at least one voice emitter on the mask.

14. A protective covering for a face screen for a mask comprising: a substantially oval thin sheet of flexible material, wherein said sheet has a first frosted side and an opposite adhesive side wherein said adhesive side is applied to the mask to cover and protect the mask.

* * * * *